United States Patent
Elsayed et al.

(10) Patent No.: US 11,478,464 B1
(45) Date of Patent: Oct. 25, 2022

(54) METHOD FOR TREATING INFLAMMATION

(71) Applicant: KING FAISAL UNIVERSITY, Al-Ahsa (SA)

(72) Inventors: Mahmoud Kandeel Elsayed, Al-Ahsa (SA); Shady Burayk, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 17/665,553

(22) Filed: Feb. 6, 2022

(51) Int. Cl.
*A61K 31/454* (2006.01)
*A61K 31/4422* (2006.01)
*A61P 29/00* (2006.01)

(52) U.S. Cl.
CPC ........ *A61K 31/454* (2013.01); *A61K 31/4422* (2013.01); *A61P 29/00* (2018.01)

(58) Field of Classification Search
CPC .... A61K 31/454; A61K 31/4422; A61P 29/00
See application file for complete search history.

(56) References Cited

U.S. PATENT DOCUMENTS

| | | | |
|---|---|---|---|
| 5,141,950 A | 8/1992 | Nakane et al. | |
| 6,566,359 B1 * | 5/2003 | Bazan | C07D 249/08 544/82 |
| 7,309,716 B2 | 12/2007 | Wilson et al. | |
| 8,138,168 B1 * | 3/2012 | Jones | C07D 409/12 546/187 |
| 2021/0267971 A1 | 9/2021 | Singh et al. | |

OTHER PUBLICATIONS

Veerasamy et al., "Structure-Activity Relationship Analysis of Benzimidazoles as Emerging Anti-Inflammatory Agents: An Overview," Pharmaceuticals, 14(663) Jul. 11, 2021.
C1: National Center for Biotechnology Information PubChem Databse CID=50981486, Published Mar. 29, 2011.
C2: National Center for Biotechnology Information PubChem Databse CID=50958415 Published Mar. 29, 2011.

* cited by examiner

*Primary Examiner* — Craig D Ricci
*Assistant Examiner* — Janet L Coppins
(74) *Attorney, Agent, or Firm* — Nath, Goldberg & Meyer; Richard C. Litman (57) ABSTRACT

A method of treating inflammation includes administering an anti-inflammatory agent to a patient in need thereof. The anti-inflammatory agent is selected from Compound 1 ([(2-{[3-(4-methyl-1H-benzimidazol-2-yl)piperidin-1-yl]carbonyl}phenyl) amino] acetic acid) and Compound 2 (Ethyl-1-(5-cyano-2-hydroxyphenyl)-4-oxo-5-phenoxy-1,4-dihydropyridine-3-carboxylate). Compound 1 and Compound 2 selectively inhibit COX-2 enzyme, without substantially inhibiting COX-1 enzyme, in contrast to many other NSAIDs.

7 Claims, 7 Drawing Sheets

METHOD FOR TREATING INFLAMMATION

BACKGROUND

1. Field

The disclosure of the present patent application relates to methods of treating inflammation using non-steroidal anti-inflammatory compounds (also known as Non-Steroidal Anti-Inflammatory Drugs—NSAIDs, or Non-Steroidal Anti-Inflammatory Agents—NSAIAs), and particularly to methods of treating inflammation using non-steroidal anti-inflammatory compounds that target cyclooxygenase-2 (COX-2) enzyme.

2. Description of the Related Art

In the treatment of inflammatory episodes, nonsteroidal anti-inflammatory medications (NSAIDs) constitute the gold standard. NSAIDs, by definition, reduce inflammation and relieve pain, but are not related to steroids (which also reduce inflammation). NSAIDs block production of certain body chemicals associated with inflammation, thereby treating pain, fever, and other inflammatory effects on the body. One of the most common NSAIDs is aspirin.

Inflammation is associated with redness, pain, and swelling. Inflammation may be acute, or it may be chronic. Some diseases are associated with chronic inflammation—such as arthritis and rheumatoid arthritis, diabetes, asthma, autoimmune diseases, Alzheimer's, and cardiovascular disease, among many others. Prostaglandins act as mediators of acute inflammation and may also play a part in chronic inflammation.

NSAIDs reduce production of prostaglandins, which play a key role in generating the inflammatory response. Specifically, NSAIDs block cyclooxygenase (COX) enzymes, which are involved in formation of prostaglandins. Inhibition of COX enzymes impairs or inhibits prostaglandin synthesis, resulting in reduction of inflammation and in associated effects of inflammation.

In this context, cyclooxygenases 1 and 2 (COX-1 and COX-2) and arachidonate 5-lipooxygenase (5-lox) play key roles in the production and regulation of inflammation. COX-1 is expressed predominantly in the gastrointestinal tract, while COX-2 is predominantly produced at sites of inflammation. The stomach lining and renal functions are protected by certain prostaglandins produced by COX-1. COX-2 is activated in response to inflammation and is, therefore, inducible in nature. The enzyme 5-lox is involved in transforming essential fatty acid substrates into leukotrienes (as well as other biologically active products). Leukotrienes (LTs) are the first class of mediators that contribute to the inflammatory process. LTs play a significant part in the inflammatory process overall.

Prostaglandin E2 (PGE2) and prostaglandin I2 (PGI2, or prostacyclin) increase blood flow in inflamed areas by their potent vasodilators action. PGI2 is responsible for platelet aggregation and vascular endothelium inhibition. The vasodilation effect of Prostaglandin E2 and Prostacyclin I2 acts to protect the gastric mucosa by increasing the secretion of mucus and preventing increase of acidity and pepsin content in the stomach. In the kidneys, PGE and PGI play a role in increasing the blood flow and regulation of the glomerular filtration rate.

Non-steroidal anti-inflammatory drugs are the gold standard in treating inflammatory episodes due to their ability to block the arachidonic acid pathways. NSAIDs act by selective or non-selective inhibition of COX-1 and COX-2 enzymes. In addition to lowering inflammation, however, non-selective medicines inhibit platelet aggregation. Additionally, the non-selective medications raise the risk of stomach ulcers and bleeding. There are fewer side effects with selective COX-2 inhibitors, and their gastrointestinal ulcerogenic properties are decreased as well.

Accordingly, development of new, selective NSAIDs that result in reduced frequency and severity of negative side effects is desired.

3. SUMMARY

A method of treating inflammation can include administering a therapeutically effective amount of an anti-inflammatory compound to a patient in need thereof, the anti-inflammatory compound being selected from the group consisting of Compound 1 ([(2-{[3-(4-methyl-1H-benzimidazol-2-yl)piperidin-1-yl]carbonyl}phenyl)amino]acetic acid) and Compound 2 (Ethyl-1-(5-cyano-2-hydroxyphenyl)-4-oxo-5-phenoxy-1,4-dihydropyridine-3-carboxylate).

Compounds 1 and 2 were demonstrated to treat paw swelling in a carrageenan-induced paw edema test. Compounds 1 and 2 also were shown to reduce inflammatory cell infiltration and alleviate edema with lesser collagen deposition in histopathological sections stained with H&E (hematoxylin and eosin) and Masson's trichrome stains. Further, Compound 1 and Compound 2 were found to particularly inhibit COX-2 and demonstrated safe profiles by having no effect on gastric mucosa integrity or mucosa collagen content. As a result, these molecules have great potential as new anti-inflammatory medicines.

These and other features of the present disclosure will become readily apparent upon further review of the following specification and drawings.

4. BRIEF DESCRIPTION OF THE DRAWINGS

FIGS. 3A to 3J show comparison of histopathologic examinations of rat paw stained by H&E stain, as follows.

Similar reference characters denote corresponding features consistently throughout the attached drawings.

5. DETAILED DESCRIPTION OF THE EMBODIMENTS

A method of treating inflammation can include administering a therapeutically effective amount of an anti-inflammatory compound to a patient in need thereof, the anti-inflammatory compound being selected from the group consisting of ([(2-{[3-(4-methyl-1H-benzimidazol-2-yl)
piperidin-1-yl]carbonyl}phenyl) amino] acetic acid) and (Ethyl-1-(5-cyano-2-hydroxyphenyl)-4-oxo-5-
phenoxy-1,4-dihydropyridine-3-carboxylate).

In an embodiment, the method can include administering a pharmaceutical composition including the anti-inflammatory compound and a pharmaceutically acceptable carrier. The phrase "pharmaceutically acceptable," as used herein, refers to molecular entities and compositions that do not produce an allergic or similar untoward reaction when administered to a human. As used herein, a "carrier" includes any and all solvents, dispersion media, vehicles, coatings, diluents, isotonic and absorption delaying agents, buffers, carrier solutions, suspensions, colloids, excipients, and the like. A therapeutically effective amount of the compound or an amount effective to treat inflammation may be determined initially from the Examples described herein and adjusted for specific targeted diseases using routine methods. The present compositions can be in unit dosage forms such as tablets, pills, capsules, powders, granules, ointments, sterile parenteral solutions or suspensions, metered aerosol or liquid sprays, drops, ampules, autoinjector devices or suppositories, for oral parenteral, intranasal, sublingual or rectal administration, or for administration by inhalation or insufflation. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose.

As described in detail below, an initial virtual screening of over one million compounds was conducted to identify candidate compounds with structures suitable for targeting the structure of proteins highly associated with inflammation. Further assessment of the candidates identified by the virtual screening was then conducted based on computational pharmacokinetic features, drug-likeness, percent of oral absorption in humans, anticipated carcinogenicity, mutagenicity, and toxicity testing. Ultimately, seven compounds were chosen for further in vitro assessment for their inhibitory effects against COX-1 and COX-2 as well as cytotoxicity studies against Human embryonic kidney (HEK293) cells based on their powerful docking score, overall safety profiles, and favorable drug-likeness features. The top two candidates (Compound 1 and Compound 2) had the highest selectivity index as indicated by the ratio of their half maximal inhibitory concentration—IC50—for COX-1 compared to COX-2 ($IC50_{COX-1}/IC50_{COX-2}$). The greater the ratio $IC50_{COX-1}/IC50_{COX-2}$ for a drug candidate, the greater the selectivity for preferentially inhibiting COX-2 compared to inhibition of COX-1. NSAID Compounds 1 and 2 were found to demonstrate particular efficacy and potency inhibiting COX-2 enzymes preferentially, minimizing inhibition of COX-1 enzymes and thus resulting in minimal gastrointestinal adverse effects associated with many other NSAIDs.

Non-selective inhibition of the COXs—both COX-1 and COX-2—such as exhibited in older NSAIDs like ibuprofen and naproxen, may lead to gastric ulcers because of the over-inhibition of COX-1. In contrast, there are no gastrointestinal adverse effects associated with selective COX-2 inhibitors like celecoxib. By focusing on the structural differences between COX-1 and COX-2, the present inventors identified Compound 1 and Compound 2 NSAIDs as compounds that particularly inhibit COX-2, thereby helping to minimize potential gastrointestinal adverse effects.

During the virtual screening, 1.65 million compounds were considered against the structures of three proteins highly associated with inflammation and its pathogenesis: COX-1, COX-2, and 5-lox. The thirty candidates with the greatest scores were then assessed for computational pharmacokinetic features, drug-likeness, percent of oral absorption in humans, anticipated carcinogenicity, mutagenicity, and toxicity testing. All compounds demonstrated drug-like characteristics and excellent pharmacokinetic features. However, only seven compounds were devoid of anticipated carcinogenicity in mice and rats, with a high oral absorption rate and no violations of Lipinski's rule of five. Lipinski's rule of five is used as a convenient aid in determining orally bioavailable drugs, helping to determine a candidate compound's drug-likeness and whether it is likely to be an orally active drug in humans. The seven compounds showing high binding scores in vitro for all three proteins, were then further assessed for their relative inhibitory effects specifically against COX-1 and COX-2, as well as cytotoxicity studies against human embryonic kidney (HEK293) cells based on their powerful docking score, overall safety profiles, and favorable drug-likeness features. The compounds demonstrated safety profiles and no cytotoxicity.

After 25 hours of treatment, none of these seven chemicals at a concentration of 40 μM induced obvious morphological abnormalities or damages in HEK293 cells in a cytotoxicity assay. Thus, the candidates were demonstrated to be safer than celecoxib at a comparable molar concentration, at least by this measure. These seven compounds were then examined for their inhibitory action on COX-1 and COX-2 as compared to reference NSAIDs indomethacin, diclofenac, celecoxib, and rofecoxib. All of the compounds were demonstrated to be potent inhibitors of the COX enzymes. Compounds 1 and 2 demonstrated the highest selectivity index as indicated by the ratio of their half maximal inhibitory concentration—IC50—for COX-1 compared to COX-2 ($IC50_{COX-1}/IC50_{COX-2}$). The greater the ratio $IC50_{COX-1}/IC50_{COX-2}$ for a drug candidate, the greater the selectivity for preferentially inhibiting COX-2 compared to inhibition of COX-1.

Compound 1 ([(2-{[3-(4-methyl-1H-benzimidazol-2-yl)piperidin-1-yl]carbonyl}phenyl) amino] acetic acid) and Compound 2 (ethyl-1-(5-cyano-2-hydroxyphenyl)-4-oxo-5-phenoxy-1,4-dihydropyridine-3-carboxylate) both proved to be excellent candidates for use as NSAIDs. The COX-1/COX-2 selectivity index of these two compounds compared to the reference compounds was as follows: celecoxib (326.6), rofecoxib (580), diclofenac (2.5), and indomethacin (1.38), Compound 1 (171.8) and Compound 2 (254.5).

Compounds 1 and 2 were demonstrated to treat paw swelling in a carrageenan-induced paw edema test, comparable to indomethacin and diclofenac. Compounds 1 and 2 also were shown to reduce inflammatory cell infiltration and alleviate edema with lesser collagen deposition in histopathological sections stained with H&E (hematoxylin and eosin) and Masson's trichrome stains. Further, Compounds 1 and 2 demonstrated safe profiles by having no effect on gastric mucosa integrity or mucosa collagen content.

The results identify Compounds 1 and 2 as two compounds with favorable drug-likeness, great selectivity against COX-2, powerful suppression of rat paw edema, safe profiles on cells, and no adverse effects on rat stomachs. As a result, these molecules have exciting potential as new anti-inflammatory medicines—new NSAIDs or NSAIAs. Table 1 identifies the formal chemical name and source for each of Compound 1 and Compound 2.

TABLE 1

Chemical name for Compound 1 and Compound 2

| Compound | Chemical name | Vendor | ID |
|---|---|---|---|
| Compound 1 | [(2-{[3-(4-methyl-1H-benzimidazol-2-yl)piperidin-1-yl]carbonyl}phenyl)amino]acetic acid | Chembridge Corporation (San Diego, CA, USA) | Compound 1 90161657 |
| Compound 2 | ethyl 1-(5-cyano-2-hydroxyphenyl)-4-oxo-5-phenoxy-1,4-dihydropyridine-3-carboxylate | Chembridge Corporation (San Diego, CA, USA) | Compound 2 35262215 |

The present teachings are illustrated by the following examples.

EXAMPLES

Example 1

Materials and Methods

The Schrodinger Maestro molecular modeling package (Schrodinger LLC, New York, USA) was used in all virtual screening modeling steps. QikProp software tools are an accurate, rapid, and simple-to-use method for predicting molecular properties. The QikProp software application compares the properties of a specified molecule with the properties of compounds found in 95 percent of commonly prescribed medications. To find any probable places between the active-site space of the receptor and the ligand, a gradable sequence of filters is used to attempt to locate them. A grid composed of different sets of fields that eventually give various correct gradings of the ligand poses while also justifying and representing the structure and features of the receptor is created.

COX-1 and COX-2 inhibitor screening assay kits were obtained from Cayman Chemical (Ann Arbor, Mich., USA).

Example 2

Identifying of COX-2 Inhibitor Structure

The protein data bank website was browsed in order to retrieve the COX-2 structural PDB ID 5IKQ. Through use of the protein preparation module in the Schrodinger Maestro molecular modeling tool, the structure was optimized for virtual screening and docking purposes. Crystallographic chemicals and water molecules were removed from the solution. The protein was protonated by the addition of polar hydrogens, and the structures were optimized and energy minimized by use of the OPLS2005 force field.

The Maestro grid-generating module was used to build the docking grids, which used the defined ligand-binding cavities in the analyzed structures as a starting point. A 20-nanometer grid was incorporated around the enzyme's active site.

Standard precision docking (SP) followed by extra precision docking (XP) was used in a two-step docking run to obtain the top candidates. For Van der Waals radius scaling, an integer value of 0.8 was used. Extra precision docking is designed to lower the likelihood of a false-positive result. High docking-score compounds (<–12) were chosen for interaction study with pocket residues, and their binding properties and pocket filling pattern were studied visually.

After the two-step virtual screening, Compounds 1 and 2 were selected based on their exhibiting the highest docking scores (>–13.00) supported by favorable Evdw, Hbond and Lipo scores. See Table 2. Compound 1 presented a docking score of –13.645 kcal/mol; an Evdw score of –13.963 kcal/mol; and Hbond and Lipo scores of –0.908 and –3.705, respectively, along with a ligand efficiency of –0.471. Compound 2 presented a docking score of –13.517 kcal/mol; an Evdw score of –42.204 kcal/mol; and Hbond and Lipo scores of –0.172 and –5.079, respectively, along with a ligand efficiency of –0.444.

TABLE 2

Docking Score of Compounds 1 and 2 With Cox-2 (PDB: 5IKQ).

| compound | Name | Docking Score (kcal/mol) | Glide Evdw (kcal/mol) | Glide Hbond | Glide Lipo | Glide Ligand Efficiency |
|---|---|---|---|---|---|---|
| 1 | [(2-{[3-(4-methyl-1H-benzimidazol-2-yl)piperidin-1-yl]carbonyl}phenyl)amino]acetic acid | –13.645 | –13.963 | –0.908 | –3.705 | –0.471 |
| 2 | ethyl 1-(5-cyano-2-hydroxyphenyl)-4-oxo-5- | –13.517 | –42.204 | –0.172 | –5.079 | –0.444 |

TABLE 2-continued

Docking Score of Compounds 1 and 2 With Cox-2 (PDB: 5IKQ).

| compound | Name | Docking Score (kcal/mol) | Glide Evdw (kcal/mol) | Glide Hbond | Glide Lipo | Glide Ligand Efficiency |
|---|---|---|---|---|---|---|
| | phenoxy-1,4-dihydropyridine-3-carboxylate | | | | | |

Example 3

Compound Drug-Likeness and ADME Pharmacokinetic Properties and Descriptors

Descriptors used included the compound's molecular weight, hydrogen bond donor and acceptor, oral absorption percentage and Lipinski's rule of five violations. The preADMET web-based software application was used to predict carcinogenicity.

Drug likeliness and bioavailability properties of the compounds were assessed using Qikprop v4.2. Compound carcinogenicity was determined by preADMET server (https://preadmet.bmdre.kr/). All compounds passed Lipinski's rule of five without any violation with estimated high absorption rates. As reflected in Table 3, Compounds 1 and 2 were assessed for MW, Donor and Accept HB, Human oral absorption percentage, violations of Lipinski's rule of five, and carcinogenicity in mice and rats.

TABLE 3

Drug-likeness and ADME properties of compound 1 and 2.

| | Compound 1 | Compound 2 |
|---|---|---|
| MW | 392.457 | 376.372 |
| Donor HB | 2 | 2 |
| Accept HB | 6.5 | 6.45 |
| Human oral absorption % | 91.392 | 63.711 |
| Violations of the Rule of five | 0 | 0 |
| Carcinogenicity in mouse | negative | negative |
| Carcinogenicity in rat | negative | negative |

Example 3

Cytotoxicity Evaluation by Measurement of Viability on Human Embryonic Kidney Cells 293

Human embryonic kidney cells (HEK293 cells) were cultivated in Dulbecco's modified Eagle medium (DMEM) to promote cell proliferation. HEK293 cells were treated with the compound solution at 40 µM or the vehicle dimethyl sulfoxide (DMSO) for 24 hours, with the addition of 5% fetal ox-like serum for recognition of cell feasibility reliant on mitochondrial movement. The tested compounds were Compound 1, Compound 2, diclofenac, and celecoxib.

Three wells were tested for each treatment. WST-1 reagent was added to each well, and the cells were incubated at 37° C. The difference in absorbance between 450 and 620 nm was calculated as a cell feasibility indicator.

In this manner, the effects of Compounds 1 and 2 on cell viability and proliferation were measured. Only celecoxib as a selective COX-2 inhibitor caused changes and damages in HEK293 cells among the compounds studied. In HEK293 cells, no other compounds caused damage or morphological changes at 40 µM. Table 4 sets forth the results from this analysis.

TABLE 4

Effect of Compounds 1 and 2 at 40 µm Concentration on Proliferation of Human Embryonic Kidney Cells (HEK293), Compared to Diclofenac and Celecoxib

| | HEK293 | | | Average | SD |
|---|---|---|---|---|---|
| Control (DMSO) | 1.064 | 1.0695 | 1.0584 | 1.06 | 0.01 |
| Compound 1 | 1.0653 | 1.0573 | 1.0547 | 1.06 | 0.01 |
| Compound 2 | 1.0667 | 1.0476 | 1.0648 | 1.06 | 0.01 |
| Diclofenac | 0.9967 | 1.0028 | 1.0057 | 1 | 0 |
| Celecoxib | 0.958 | 0.9688 | 0.958 | 0.96 | 0.01 |

Example 4

Enzyme (COXs) Inhibition Assay

The inhibitory effects of candidate compounds on COX-1 and COX-2 were determined using COX inhibitor screening test kits, testing each compound's capacity to inhibit the conversion of arachidonic acid to prostaglandin. In test tubes, 25 mM Tris-HCl, pH 8.0, containing 5 mM EDTA, phenol, and 1 mM hematin was added. The test compounds were dissolved in DMSO and added in concentrations ranging from 0.005-200 µM. Dimethyl sulfoxide alone was applied to control test containers. COX-1 or COX-2 enzymes were added to the test tubes, which were then preincubated for 10 minutes at 37° C. The arachidonic acid substrate was added, and the tubes were further incubated at 37° C. for 2 minutes. The compound's immunochemical assay was used to calculate the amount of prostaglandin produced.

Three separate experiments were used to calculate the IC50 values. The selectivity index was calculated as follows:

$$\text{Selectivity Index } (SI) = \frac{IC_{50}COX\text{-}1}{IC_{50}COX\text{-}2}$$

Compounds 1 and 2 inhibited the COX enzymes with compound 1 $IC_{50}$ values of 11.68±1.2 µM and 0.068±0.008 µM for COX-1 and COX-2, respectively. Accordingly, the SI for Compound 1 was 124.5 and 68.7-fold higher than the SIs for indomethacin and diclofenac, respectively. The $IC_{50}$ values for Compound 2 were 12.22±1.1 µM and 0.048±0.002 µM for COX-1 and COX-2, respectively. Thus, Compound 2 has a selectivity index of 254.5. The SI for Compound 2 was higher than that for Compound 1, making it a more selective COX-2 inhibitor (Table 5).

TABLE 5

Estimated IC50 Values (in μM) For Compounds 1 and 2
Against COX-1 and COX-2. Celecoxib, rofecoxib,
indomethacin and diclofenac were control drugs

| Compound | COX-1 IC$_{50}$ (μM) | COX-2 IC$_{50}$ (μM) | SI |
|---|---|---|---|
| Celecoxib | 14.7 ± 1.045 | 0.045 ± 0.005 | 326.6 |
| Rofecoxib | 14.5 ± 1.125 | 0.025 ± 0.005 | 580 |
| Indomethacin | 0.1 ± 0.015 | 0.0725 ± 0.01 | 1.38 |
| Diclofenac | 0.05 ± 0.006 | 0.02 ± 0.001 | 2.5 |
| Compound 1 | 11.68 ± 1.2 | 0.068 ± 0.008 | 171.8 |
| Compound 2 | 12.22 ± 1.1 | 0.048 ± 0.002 | 254.5 |

Example 5

Evaluation of Anti-Inflammatory Action on Carrageenan-Induced Paw Edema in Rats

Carrageenan was injected subcutaneously into a rodent's paw to generate inflammation due to plasma extravasation, tissue proliferation, plasma protein release, and neutrophilic extravasation, all of which are caused by arachidonic acid digestion. The major phase of inflammation occurs after the carrageenan infusion, and lasts about two hours. This primary stage is associated with the emergence of histamine and serotonin. The next stage frequently is remodeling and edema, which lasts about five hours and begins at about the third hour after administration of carrageenan. The appearance of prostaglandins, proteases, and lysosomes is associated with this second stage of inflammation.

Adult male albino rats weighing 120 g-150 g were divided into five groups of seven rats, allowed free access to food and water at 25° C. and 12 h light/dark cycle. Inflammation was generated in the rats by subplantar injection of 0.2 ml of 1% carrageenan solution in 0.9 percent saline (Sigma-Aldrich, St. Louis, Mo., USA), and injected into the right hind paw. A vernier caliper (SMIEC, Shanghai, China) was used to measure the thickness of the rat paws before and after carrageenan injection to provide a measure of the inflammation caused by carrageenan.

Compounds 1 and 2, as well as indomethacin and diclofenac sodium, were suspended individually in 1% sodium carboxymethyl cellulose (NaCMC) in normal saline and administered orally at 10 mg/kg body weight in a total volume of 1 ml/rat, with the negative control receiving only 1 ml of 1% NaCMC-saline solution (without administration of carrageenan or treating agent).

Paw edema was measured at 0 minutes, 30 minutes, and 1, 2, 3, 4, and 5 hours following administration of the medication. Inhibition of edema was indicated by the reduction of increased thickness when comparing the treated and control groups.

Example 6

Figure 1:
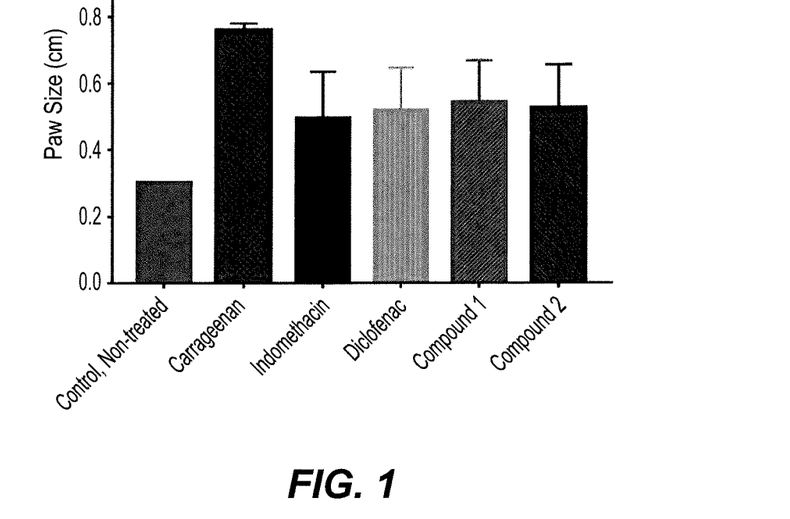
FIG. 1 is a graph showing initial average rats paw edema size, comparing the following groups: control nontreated rats (receiving NaCMC—sodium carboxymethylcellulose); control treated with 0.2 ml 1% carrageenan; and rats treated first with the carrageenan and then orally with indomethacin, diclofenac, Compound 1, or Compound 2, each at a dose rate of 10 mg/kg.

Anti-Inflammatory Actions of Compounds 1 and 2: Carrageenan-Induced Rat Paw Edema After receiving carrageenan injections, the rat paws grew from about 0.3 cm to about 0.8 cm in size. Treatment with diclofenac and indomethacin significantly reduced rat paw edema after one hour of administration (FIG. 1) Compounds 1 and 2 both showed significant decreases in rat paw size, comparable to—and without statistically significant difference from—the decreases resulting from treatment with diclofenac and indomethacin, two commonly used COX inhibitors.

Figure 2:
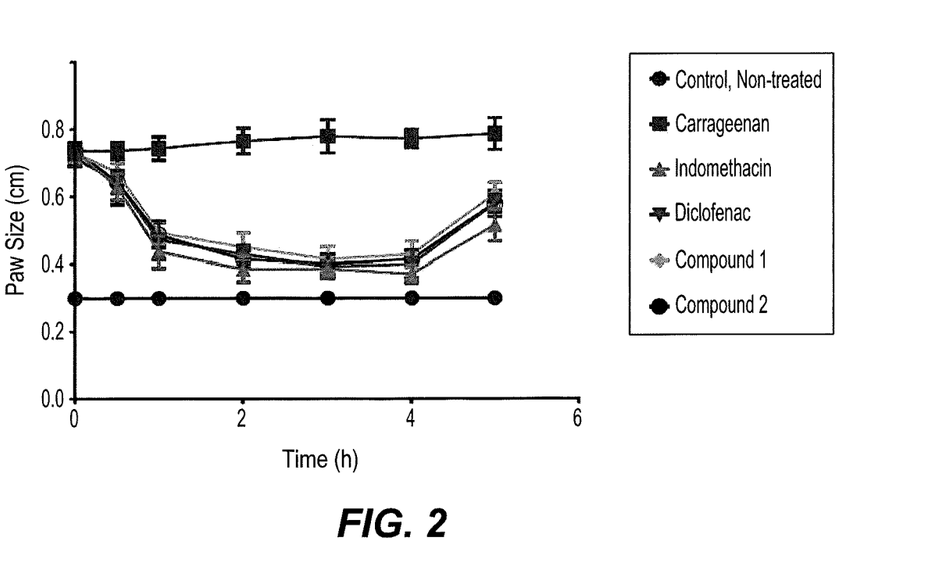
FIG. 2 is a graph showing the progress of rat paw edema size over a period of 5 hours following administration of the compounds reflected in FIG. 1. Measurements were performed at 0 and 30 minutes, and 1, 2, 3, 4, and 5 hours after administration of the compounds.

The continued progress of rat paw edema size showed a significant decrease within the first 30 minutes after administration of all treating agents (FIG. 2). The untreated paws remained about the same size throughout the 5 hours of observation. The carrageenan-treated paws receiving control treatment (NaCMC) remained at an increased size of about 0.8 cm throughout the 5 hours. For four hours following administration of active treatment, the size of the rat paw progressed in a nearly identical manner across Compound 1, Compound 2, indomethacin, and diclofenac (FIG. 2). These results are also summarized in Table 6.

TABLE 6

Rat Paw Edema Thickness for Compounds 1, Compound 2, Indomethacin and
Diclofenac in Carrageenan-Induced Paw Edema, after Oral Dosing of Compounds at 10
Mg/Kg body weight. The Control Group Received NaCMC. Measurements Performed
At 0, 30 Min, 1, 2, 3, 4 And 5 Hours After Compound Administration

| Time of measurement | Compound 1 | Compound 2 | Diclofenac | Indomethacin | Control | Normal |
|---|---|---|---|---|---|---|
|  | \multicolumn{6}{Paw size (cm)} | | | | | |
| zero time | 0.7 | 0.75 | 0.7 | 0.75 | 0.75 | 0.3 |
|  | 0.75 | 0.75 | 0.7 | 0.7 | 0.7 | 0.3 |
|  | 0.7 | 0.75 | 0.7 | 0.75 | 0.75 | 0.3 |
|  | 0.75 | 0.75 | 0.7 | 0.75 | 0.75 | 0.3 |
|  | 0.75 | 0.7 | 0.75 | 0.7 | 0.75 | 0.3 |
|  | 0.75 | 0.75 | 0.7 | 0.75 | 0.75 | 0.3 |
|  | 0.7 | 0.7 | 0.75 | 0.75 | 0.7 | 0.3 |
| 30 min | 0.7 | 0.7 | 0.7 | 0.7 | 0.75 | 0.3 |
|  | 0.7 | 0.65 | 0.65 | 0.6 | 0.75 | 0.3 |
|  | 0.65 | 0.55 | 0.6 | 0.6 | 0.75 | 0.3 |
|  | 0.65 | 0.7 | 0.65 | 0.65 | 0.7 | 0.3 |
|  | 0.7 | 0.7 | 0.65 | 0.6 | 0.75 | 0.3 |
|  | 0.65 | 0.65 | 0.6 | 0.6 | 0.75 | 0.3 |
|  | 0.65 | 0.55 | 0.65 | 0.65 | 0.7 | 0.3 |
| 1 hour | 0.55 | 0.55 | 0.55 | 0.5 | 0.75 | 0.3 |
|  | 0.5 | 0.5 | 0.5 | 0.4 | 0.7 | 0.3 |
|  | 0.5 | 0.45 | 0.4 | 0.45 | 0.75 | 0.3 |
|  | 0.45 | 0.45 | 0.45 | 0.4 | 0.75 | 0.3 |
|  | 0.5 | 0.5 | 0.5 | 0.4 | 0.7 | 0.3 |
|  | 0.5 | 0.5 | 0.4 | 0.5 | 0.75 | 0.3 |
|  | 0.45 | 0.45 | 0.5 | 0.4 | 0.8 | 0.3 |
| 2 hours | 0.5 | 0.45 | 0.45 | 0.45 | 0.8 | 0.3 |
|  | 0.45 | 0.4 | 0.4 | 0.4 | 0.75 | 0.3 |

TABLE 6-continued

Rat Paw Edema Thickness for Compounds 1, Compound 2, Indomethacin and Diclofenac in Carrageenan-Induced Paw Edema, after Oral Dosing of Compounds at 10 Mg/Kg body weight. The Control Group Received NaCMC. Measurements Performed At 0, 30 Min, 1, 2, 3, 4 And 5 Hours After Compound Administration

| Time of measurement | Compound 1 | Compound 2 | Diclofenac | Indomethacin | Control | Normal |
|---|---|---|---|---|---|---|
| | | | Paw size (cm) | | | |
| | 0.45 | 0.4 | 0.4 | 0.35 | 0.7 | 0.3 |
| | 0.4 | 0.4 | 0.45 | 0.35 | 0.75 | 0.3 |
| | 0.45 | 0.4 | 0.45 | 0.4 | 0.8 | 0.3 |
| | 0.5 | 0.4 | 0.4 | 0.4 | 0.8 | 0.3 |
| | 0.4 | 0.45 | 0.45 | 0.35 | 0.75 | 0.3 |
| 3 hours | 0.4 | 0.35 | 0.4 | 0.4 | 0.85 | 0.3 |
| | 0.35 | 0.4 | 0.4 | 0.4 | 0.75 | 0.3 |
| | 0.4 | 0.4 | 0.35 | 0.35 | 0.7 | 0.3 |
| | 0.45 | 0.4 | 0.4 | 0.4 | 0.75 | 0.3 |
| | 0.45 | 0.45 | 0.45 | 0.4 | 0.8 | 0.3 |
| | 0.4 | 0.4 | 0.35 | 0.35 | 0.8 | 0.3 |
| | 0.45 | 0.4 | 0.4 | 0.4 | 0.8 | 0.3 |
| 4 hours | 0.45 | 0.4 | 0.35 | 0.35 | 0.75 | 0.3 |
| | 0.4 | 0.45 | 0.4 | 0.4 | 0.8 | 0.3 |
| | 0.4 | 0.4 | 0.45 | 0.35 | 0.8 | 0.3 |
| | 0.45 | 0.4 | 0.35 | 0.35 | 0.8 | 0.3 |
| | 0.4 | 0.4 | 0.4 | 0.4 | 0.75 | 0.3 |
| | 0.4 | 0.4 | 0.45 | 0.35 | 0.75 | 0.3 |
| | 0.5 | 0.45 | 0.4 | 0.4 | 0.75 | 0.3 |
| 5 hours | 0.55 | 0.55 | 0.55 | 0.5 | 0.85 | 0.3 |
| | 0.6 | 0.6 | 0.6 | 0.55 | 0.75 | 0.3 |
| | 0.6 | 0.6 | 0.55 | 0.45 | 0.75 | 0.3 |
| | 0.6 | 0.6 | 0.6 | 0.55 | 0.75 | 0.3 |
| | 0.65 | 0.5 | 0.6 | 0.55 | 0.85 | 0.3 |
| | 0.6 | 0.6 | 0.55 | 0.45 | 0.8 | 0.3 |
| | 0.65 | 0.6 | 0.6 | 0.55 | 0.75 | 0.3 |
| Average | 0.542 | 0.524 | 0.518 | 0.494 | 0.759 | 0.300 |

The rat paws were removed and promptly cleaned in saline solution. The specimens were then fixed in 10% natural formalin for two days, and then rinsed with running water overnight. The cleaned samples were then dehydrated in increasing concentrations of ethyl alcohol, beginning with 70% and ending with absolute alcohol.

The samples were cleared by soaking them in xylol for 2 hours. The cleared samples were placed in a covered jar containing 50% paraffin in xylol for 3 hours at 37° C. The samples were then immersed in melting paraffin and maintained at 48° C. for 2 hours before being blocked in hard paraffin and cut into 5-micron sections. Hematoxylin and eosin (H&E) and Masson's trichrome were used to stain the sections. To prepare for histopathological investigation, sections of control rat paws, as well as rat paws treated with carrageenan alone or along with Compound 1, Compound 2, or indomethacin, were mounted with Canada balsam and coated with a coverslip.

Figure 3A:
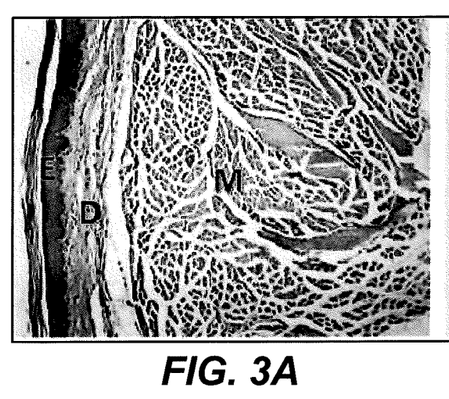
FIG. 3A is a photomicrograph of control rat paw at 10× magnification, showing normal epidermal layers (E), dermis (D), and muscle layer (M)
Figure 3B:
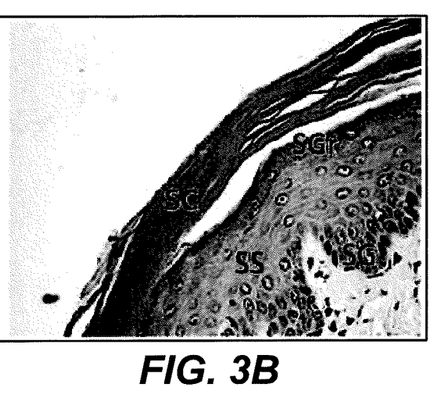
FIG. 3B is a photomicrograph of control rat paw at 40× magnification, showing normal stratum corneum (SC), stratum granulosum (SGr), stratum spinosum (SS), and stratum germinativum (SG)
Figure 3C:
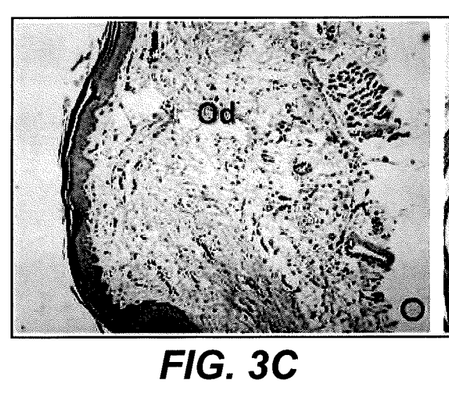
FIG. 3C is a photomicrograph of rat paw at 10× magnification after carrageenan treatment, showing marked thickening of the dermal layer, inflammatory reaction in the deep dermis, and wide separation between fibers, due to edema (Od)
Figure 3D:
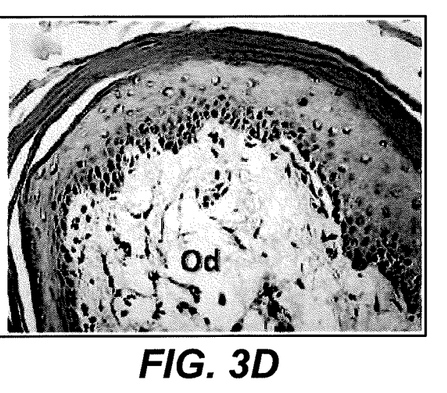
FIG. 3D is a photomicrograph of rat paw at 40× magnification after carrageenan treatment, showing edema (Od)

FIGS. 3A to 3J show photomicrographs of exemplary rat paw sections under varying magnifications after treatment with H&E stain. The control group sections of rat paw displayed a healthy paw tissue structure, exhibiting a typical intact epidermal layer of stratified squamous epithelium and dermal layer with ample capillaries and connective tissue cells. FIG. 3A is a 10× magnification, showing normal epidermal layers (E), dermis (D), and muscle layer (M), with the absence of any signs of inflammatory reaction. FIG. 3B is a 40× magnification, showing normal stratum corneum (SC), stratum granulosum (SGr), stratum spinosum (SS), and stratum germinativum (SG). In contrast, the carrageenan-injected paw tissue sections showed substantial histopathological changes. These included increased dermis thickness attributable to edema (Od) with a markedly inflammatory cell invasion of the deep dermis and wide separation between fibers compared to the control group. See FIGS. 3C (10× magnification) and 3D (40× magnification).

Figure 3E:
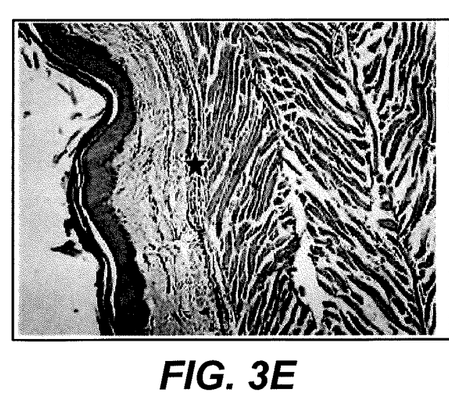
FIG. 3E is a photomicrograph of rat paw at 10× magnification after carrageenan treatment followed by administration of compound 1, showing significant decrease in dermal thickness, inflammatory reaction in the deep dermis (black star), and moderate improvement in edema.
Figure 3F:
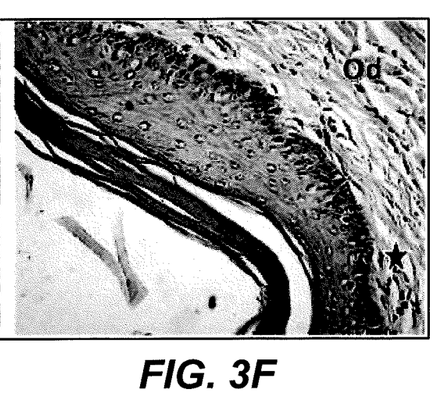
FIG. 3F is a photomicrograph of rat paw at 40× magnification after carrageenan treatment followed by administration of compound 1, showing slight inflammatory reaction (black star) and slight edema (Od)
Figure 3G:
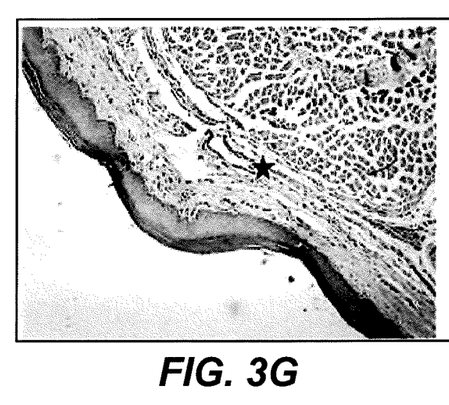
FIG. 3G is a photomicrograph of rat paw at 10× magnification after carrageenan treatment followed by administration of Compound 2, showing substantial decrease in both inflammatory reaction (black star) and edema.
Figure 3H:
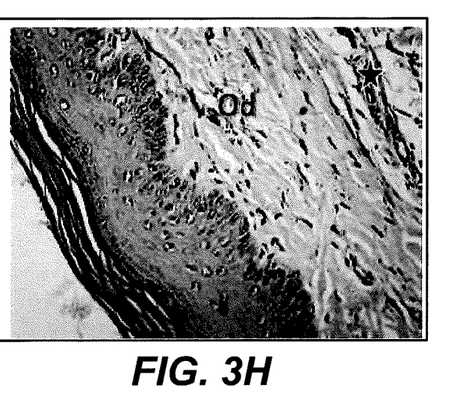
FIG. 3H is a photomicrograph of rat paw at 40× magnification after carrageenan treatment followed by administration of Compound 2, showing slight inflammatory reaction (black star) and slight edema (Od)

The rat paws treated with the various treating agents exhibited improvements in the inflammatory conditions caused by the carrageenan. The rat paws treated with Compound 1 exhibited marked improvement in the degree of edema and the inflammatory cell infiltration. FIGS. 3E (10× magnification) and 3F (40× magnification) show improvement after treatment with Compound 1, with significantly decreased dermal thickness and inflammatory reaction in the deep dermis (black star), and moderate improvements in edema (Od). Similarly, rat paws treated with Compound 2 demonstrated a substantial decrease in both inflammatory reaction (black star) and a pronounced decline in edema (Od) (FIGS. 3G (10× magnification) and 3H (40× magnification)).

Figure 3I:
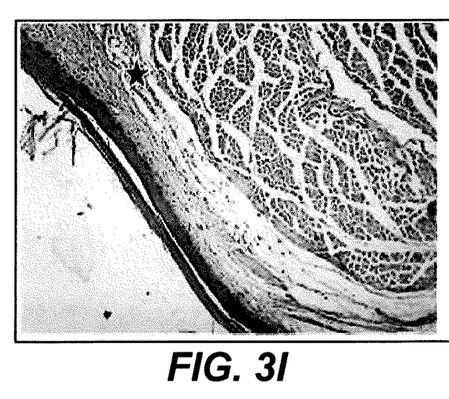
FIG. 3I is a photomicrograph of rat paw at 10× magnification after carrageenan treatment followed by administration of indomethacin, showing significant decrease in inflammatory reaction (black star) and a moderate decrease in edema (Od)
Figure 3J:
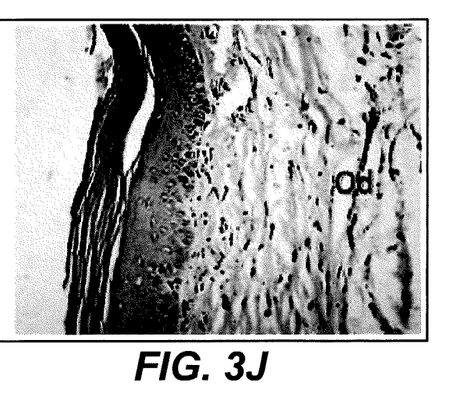
FIG. 3J is a photomicrograph of rat paw at 40× magnification after carrageenan treatment followed by administration of indomethacin, showing slight inflammatory reaction (black star) and slight edema (Od).

Similarly, the rat paws treated with indomethacin showed a significant decrease in the degree of inflammatory reaction (black star), and a moderate decrease in edema (Od) (FIGS. 3I (10× magnification) and 3J (40× magnification)).

The degree of collagen deposition was investigated by Masson's stain as a qualitative indicator. Blue-green stained collagen was used for the purpose of assessing collagen deposition progression; the cytoplasm, red blood cells, and muscle were stained red. The density of the blue-green collagen is consistent with the relative amount of deposited total collagen fiber, which represents collagen synthesis, degradation, and remodeling—some of which is associated with inflammation.

Figure 4A:
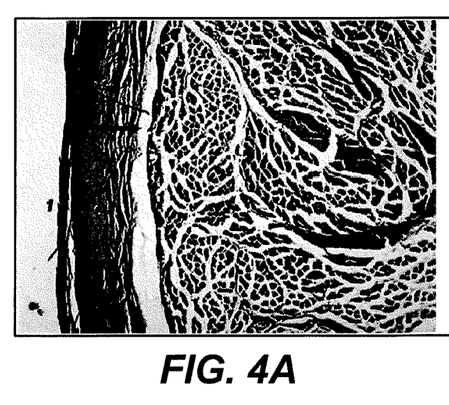
FIGS. 4A to 4E are a series of comparative photomicrographs resulting from histopathologic examination of rat paw administered various treatments and stained by Masson's Trichrome stain, where the double headed arrow represents collagen fibrils thickness between epidermis and dermis, as follows: (4A) is the control rat paw at 10× magnification showing normal collagen deposition; (4B) is the carrageenan-treated rat paw at 10× magnification showing intense collagen deposition; (4C) is a carrageenan-treated rat paw after treatment with compound 1, at 10× magnification showing slight collagen deposition; (4D) is a carrageenan-treated rat paw after treatment with Compound 2, at 10× magnification showing slight collagen deposition; (4E) is a carrageenan-treated rat paw after treatment with indomethacin, at 10× magnification showing slight collagen deposition.
Figure 4B:
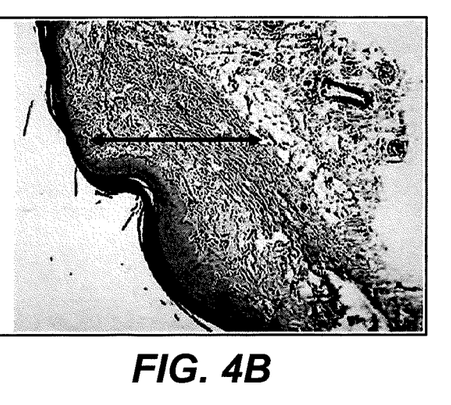
Figure 4C:
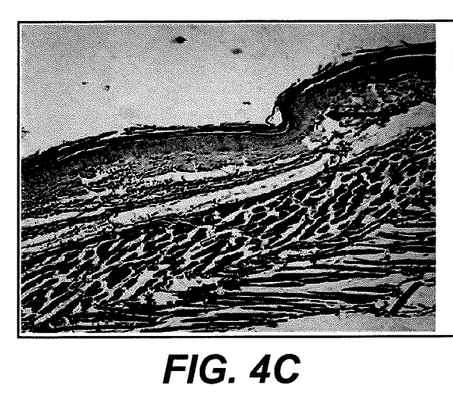
Figure 4D:
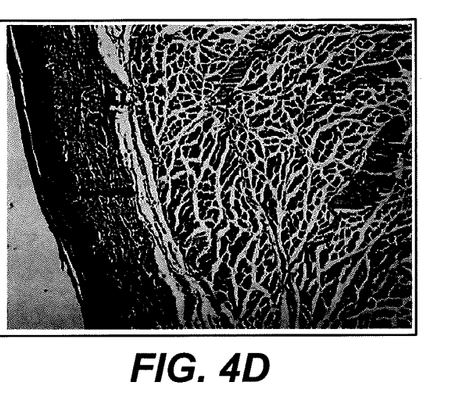
Figure 4E:
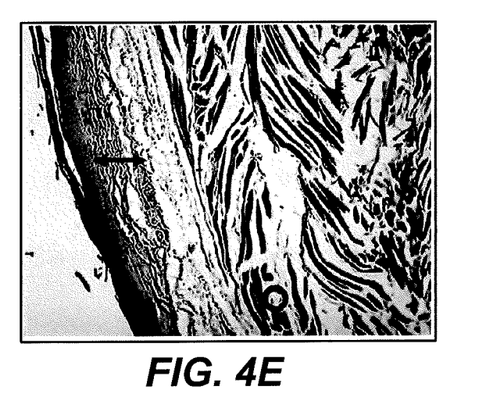

As shown by Masson's stain, there were more collagen fibers in the carrageenan group (FIG. 4B, 10× magnification) compared with the normal group (FIG. 4A, 10× magnification). In FIGS. 4A to 4E, the double-headed arrow represents collagen fibrils thickness between epidermis and dermis. Among the three treated groups, the collagen deposition was almost similar to the control nontreated group. The rat paws treated with Compound 1 showed slight collagen deposition (FIG. 4C (10× magnification)). Similarly, the rat paws treated with Compound 2 showed slight collagen deposition, (FIG. 4D (10× magnification)), as did the rat paws treated with indomethacin (FIG. 4E (10× magnification)).

The quantity of collagen formation was the lowest in the Compound 2-treated group and thus was better than in the indomethacin-treated group.

Example 7

Evaluation of Ulcerogenic Effect by the Test Compounds on Rat Stomach

Compounds 1 and 2 showed anti-inflammatory benefits as discussed above. These compounds were also tested for ulcerogenic effects in the rat stomach.

Rats were starved for 24 hours at a normal room temperature of 25° C. with a 12-hour light/dark cycle. The reference drug for comparison was indomethacin. All compounds were administered orally at a single dose of 20 mg/kg. The rats were sacrificed after 24 hours, and their stomachs were retrieved and cleansed with normal saline. Each group's stomachs were examined using binocular magnification to detect the presence of a gastric lesion on the mucosa. The stomachs were then preserved in 10% w/v formalin for histological analysis. Exemplary photomicrographs are included in FIGS. 5A to 5H, and FIGS. 6A to 6H, as discussed further below.

Figure 5A:
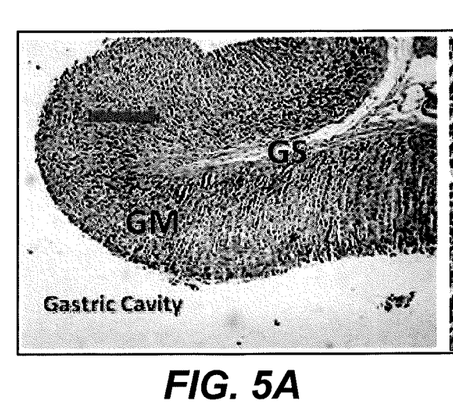
FIGS. 5A to 5H are a series of comparative photomicrographs resulting from histopathologic examination of rat stomach administered various treatments and stained by H&E, as follows: (5A) is the control rat stomach at 10× magnification, showing normal gastric layers and the arrow indicating intact appearance of histological structure of the epithelium and mucosa layer, gastric mucosa (GM), and gastric submucosa (GS); (5B) is the control rat stomach at 40× magnification, showing absence of inflammatory reaction; (5C) is a rat stomach at 10× magnification after treatment with compound 1, showing normal gastric layers and the arrow indicating intact appearance of the epithelium and mucosa layer, gastric mucosa (GM), and gastric submucosa (GS); (5D) is a rat stomach at 40× magnification after treatment with compound 1, showing absence of any inflammatory reaction; (5E) is a rat stomach at 10× magnification after treatment with Compound 2, showing normal gastric layers and the arrow indicating intact appearance of the epithelium and mucosa layer, gastric mucosa (GM), and gastric submucosa (GS); (5F) is a rat stomach at 40× magnification after treatment with Compound 2, showing absence of any inflammatory reaction; (5G) is a rat stomach at 10× magnification after treatment with indomethacin, showing slight degeneration of gastric layers and the arrow indicating intact appearance of the epithelium and mucosa layer, gastric mucosa (GM), and gastric submucosa (GS); (5H) is a rat stomach at 40× magnification after treatment with indomethacin, showing absence of any inflammatory reaction.
Figure 5B:
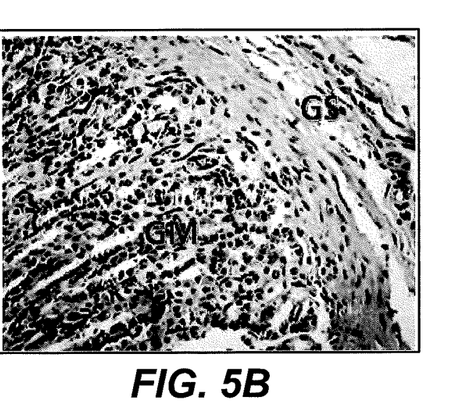
Figure 5C:
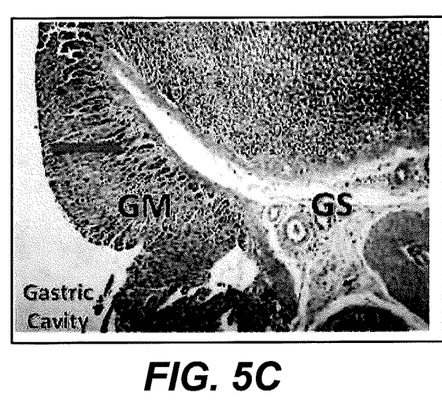
Figure 5D:
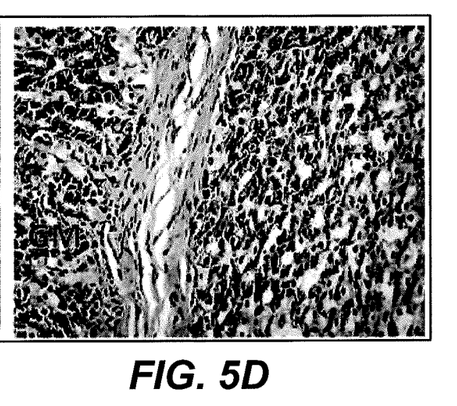
Figure 5E:
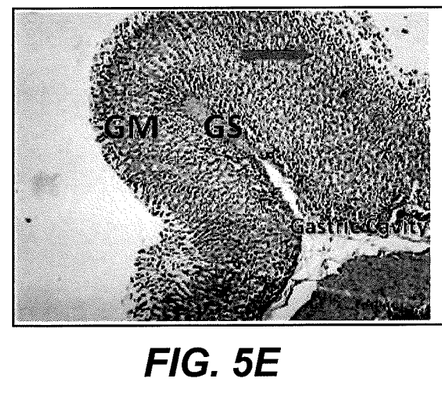
Figure 5F:
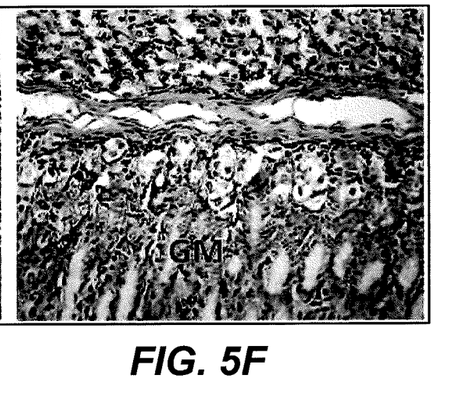
Figure 5G:
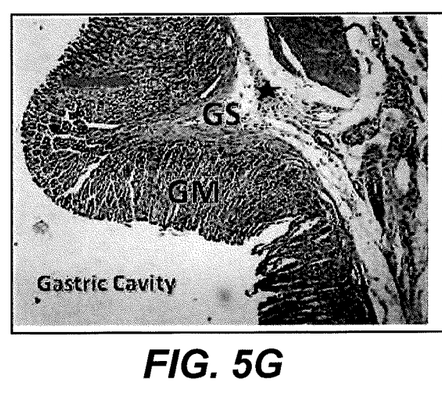
Figure 5H:
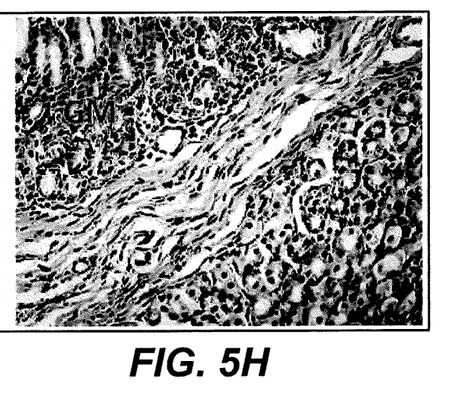

The control group stomach sections displayed a healthy gastric tissue structure exhibiting typical intact villi of gastric mucosa with no signs of hemorrhage or congestion. Exfoliation in the mucosal epithelium or appearance of inflammatory cell infiltration were also not detected. FIG. 5A is a 10× magnification showing a control rat stomach, with normal gastric layers; intact appearance of histological structure of the epithelium and mucosa layer (blue arrow), the gastric mucosa (GM), and gastric submucosa (GS). FIG. 5B is a 40× magnification showing the absence of any signs of inflammatory reaction.

The Compound 1 treatment showed normal gastric layers, and intact appearance of the epithelium and mucosa layer (blue arrow), gastric mucosa (GM), and gastric submucosa (GS). See FIG. 5C (10× magnification). Even at 40× magnification, there is no sign of inflammatory reaction. See FIG. 5D (40× magnification). Treatment with Compound 2 similarly reflects normal gastric layers, including intact epithelium and mucosa layer (blue arrow), gastric mucosa (GM), and gastric submucosa (GS). See FIG. 5E (10× magnification). Again, even at 40× magnification, the Compound 2-treated rat stomachs show no sign of inflammatory reaction. See FIG. 5F (40× magnification).

In contrast, the indomethacin-treated rat stomachs showed a slight degeneration of gastric layers, indicated by the appearance of the epithelium and mucosa layer (blue arrow), the gastric mucosa (GM), and the gastric submucosa (GS). See FIG. 5G (10× magnification). However, at 40× magnification, there is no sign of inflammatory reaction in the indomethacin-treated stomachs. See FIG. 5H.

The rat stomachs were also examined with regard to collagen deposition. This was accomplished by histopathologic examination of rat stomachs stained by Masson's Trichrome stain. See the photomicrographs of exemplary sections depicted in FIGS. 6A to 6H. Again, after application of Masson's Trichrome, the collagen fibrils are stained blue-green. The double-headed arrow represents collagen fibrils thickness in the submucosa.

Figure 6A:
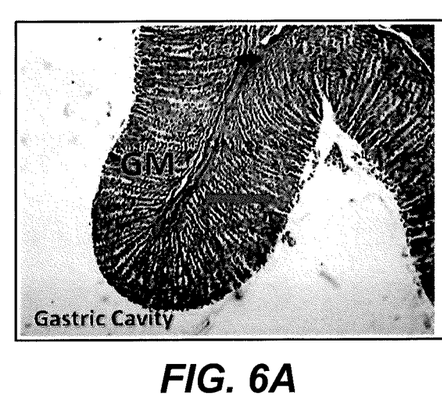
FIGS. 6A to 6H are a series of comparative photomicrographs resulting from histopathologic examination of rat stomach administered various treatments and stained by Masson's Trichrome stain, where the double headed arrow represents collagen fibrils thickness in the submucosa, as follows: (6A) is a control rat stomach at 10× magnification, showing normal collagen deposition; (6B) is a control rat stomach at 40× magnification, showing normal collagen deposition; (6C) is a rat stomach after treatment with compound 1, at 10× magnification showing normal collagen deposition; (6D) is a rat stomach after treatment with compound 1, at 40× magnification showing normal collagen deposition; (6E) is a rat stomach after treatment with Compound 2, at 10× magnification showing slight collagen deposition; (6F) is a rat stomach after treatment with Compound 2, at 40× magnification showing slight collagen deposition; (6G) is a rat stomach after treatment with indomethacin, at 10× magnification showing significant collagen deposition; (6H) is a rat stomach after treatment with indomethacin, at 40× magnification showing collagen deposition.
Figure 6B:
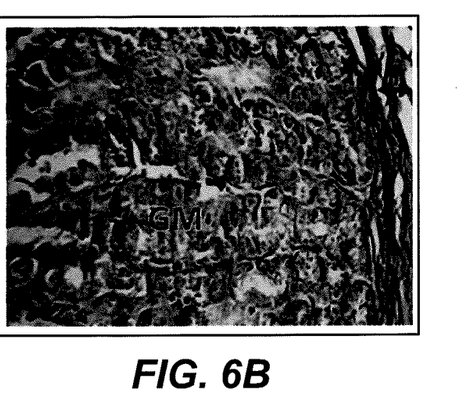
Figure 6C:
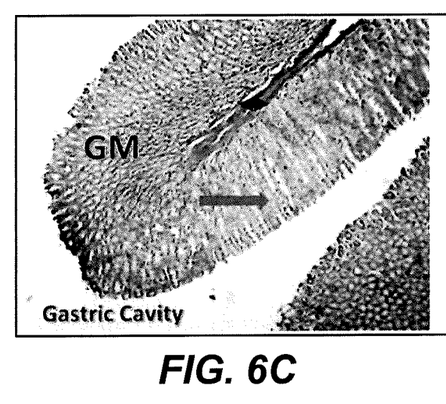
Figure 6D:
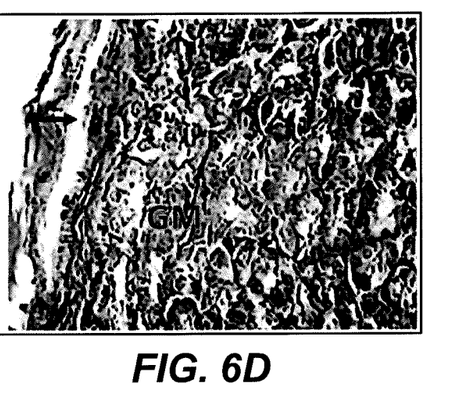
Figure 6E:
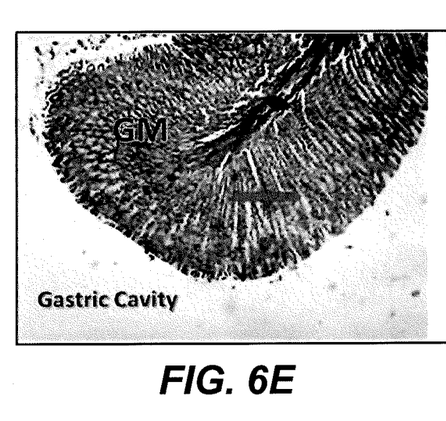
Figure 6F:
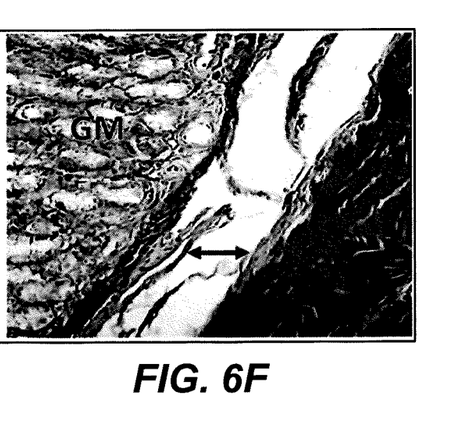
Figure 6G:
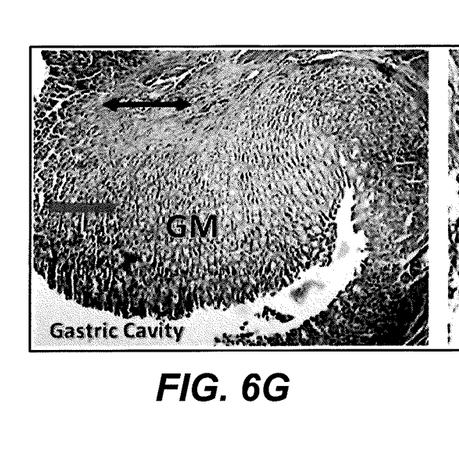
Figure 6H:
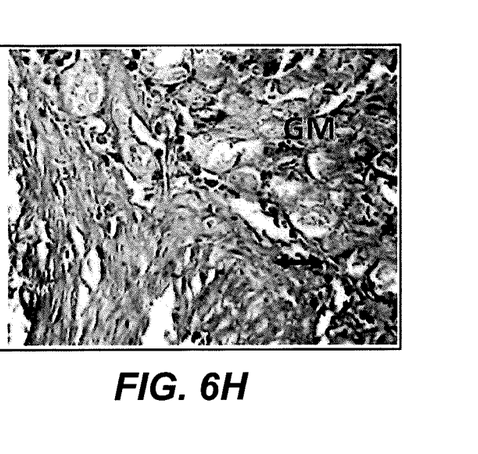

The control rat stomach group showed normal collagen deposition. FIG. 6A (10× magnification); FIG. 6B (40× magnification). The rat stomachs after treatment with Compound 1 similarly showed normal collagen deposition. FIG. 6C (10× magnification); FIG. 6D (40× magnification). After treatment with Compound 2, the rat stomachs show slight collagen deposition. FIG. 6E (10× magnification) and FIG. 6F (40× magnification). Treatment with indomethacin resulted in significant collagen deposition in the rat stomachs. FIG. 6G (10× magnification) and FIG. 6H (40× magnification).

A key feature of inflammation is the complex interplay between wounded tissues and inflammatory cells, which leads to the release of inflammatory mediators, including interleukins, necrotic factors, and enzymes like cyclooxygenases and lipoxygenases. During the inflammatory processes, the over-expression of COX-1 and COX-2 is critical for inflammatory signaling pathways. Excessive harm from an overzealous immune response or the development of chronic illness can be avoided by controlling inflammation.

Compounds 1 and 2 were compared to selective and nonselective COX inhibitors for anti-inflammatory efficacy. Compounds 1 and 2 had weaker inhibitory activities against COX-1 than indomethacin and diclofenac. Compound 2 was more effective against COX-2 than indomethacin and comparable to celecoxib. The overall selectivity index was in the following order:

rofecoxib>celecoxib>Compound 2>Compound 1>diclofenac>indomethacin.

As detailed above, the anti-inflammatory effects of the compounds were assessed using the carrageenan-induced rat paw swelling test. Carrageenan promotes exudate release and swelling due to the up-regulation of COX-2 expression, making this model ideal for testing COX-2 inhibitors. The acute carrageenan-induced inflammation in the rat paw matches the results of the in vitro enzymatic studies. After treatment with Compounds 1 and 2, indomethacin, and celecoxib, rat paw edema was dramatically reduced.

There are two stages of rat paw edema. The first stage lasts for two hours and includes the release of histamine and serotonin. Inflammatory exudate and enzymes such as cyclooxygenases are released and cells are infiltrated during the second stage, which lasts for several hours. As a result, the observed effect of Compounds 1 and 2 after 1-4 hours of inflammation is compatible with cyclooxygenase (COX) inhibitory function.

These findings support the use of Compounds 1 and 2 as anti-inflammatory agents. They are devoid of side effects on gastric mucosa and may be devoid of potential impacts on the body due to the degree of selectivity for COX-2 inhibition.

It is to be understood that the method of treating inflammation described herein is not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of treating inflammation, comprising administering a therapeutically effective amount of a pharmaceutical composition comprising an anti-inflammatory compound and a pharmaceutically acceptable carrier, the anti-inflammatory compound being selected from the group consisting of:

and

2. The method of claim 1, wherein the anti-inflammatory compound selectively inhibits cyclooxygenase 2 (COX-2).

3. The method of claim 1, wherein the compound is administered orally.

4. The method of claim 1, wherein the compound is

5. The method of claim 4, wherein the anti-inflammatory compound is administered orally.

6. The method of claim 1, wherein the anti-inflammatory compound is

7. The method of claim 6, wherein the anti-inflammatory compound is administered orally.

* * * * *